United States Patent
Pitt

(10) Patent No.: US 8,270,568 B2
(45) Date of Patent: Sep. 18, 2012

(54) APPARATUS FOR RESPIRATION STATE GATED BRACHYTHERAPY

(75) Inventor: William Robert Pitt, Horsham (GB)

(73) Assignee: Elekta AB (Publ), Stockholm (SE)

( * ) Notice: Subject to any disclaimer, the term of this patent is extended or adjusted under 35 U.S.C. 154(b) by 191 days.

(21) Appl. No.: 12/809,247

(22) PCT Filed: Dec. 21, 2007

(86) PCT No.: PCT/EP2007/011367
§ 371 (c)(1),
(2), (4) Date: Jun. 18, 2010

(87) PCT Pub. No.: WO2009/080085
PCT Pub. Date: Jul. 2, 2009

(65) Prior Publication Data
US 2010/0278306 A1    Nov. 4, 2010

(51) Int. Cl.
*A61N 5/10* (2006.01)
(52) U.S. Cl. .............................. 378/65; 378/20
(58) Field of Classification Search .................. None
See application file for complete search history.

(56) References Cited

U.S. PATENT DOCUMENTS

| | | | |
|---|---|---|---|
| 2002/0115923 A1 | 8/2002 | Erbel | 600/407 |
| 2004/0260142 A1 | 12/2004 | Lovoi | 600/1 |
| 2009/0052623 A1* | 2/2009 | Tome et al. | 378/65 |
| 2010/0317968 A1* | 12/2010 | Wright et al. | 600/427 |

FOREIGN PATENT DOCUMENTS
WO    WO 98/52635 A    11/1998

OTHER PUBLICATIONS

International Searching Authority, European Patent Office, International Search Report and Written Opinion pertaining to International application No. PCT/EP2007/011367, dated Oct. 30, 2008, 15 pages.

* cited by examiner

*Primary Examiner* — Hoon Song
(74) *Attorney, Agent, or Firm* — Sunstein Kann Murphy & Timbers LLP

(57) ABSTRACT

During treatment by brachytherapy, radiation passes beyond the target volume and delivers radiation dose to adjacent tissue such as the lungs and, especially in the case of treatment of the left breast, to the heart. The heart is particularly vulnerable to radiation; to minimise the dose it receives in such circumstances, we propose an apparatus for treatment by brachytherapy comprising an X-ray source sized for insertion into a patient, a respiration state monitor, and a control apparatus adapted to receive respiration state information from the respiration state monitor and control the output of the X-ray source; the control apparatus being arranged to operate the X-ray source at a first output level when the respiration state monitor indicates a degree of lung inflation above a first preset threshold and operate the X-ray source at a second and lower output level when the respiration state monitor indicates a degree of lung inflation below a second preset threshold.

8 Claims, 2 Drawing Sheets

APPARATUS FOR RESPIRATION STATE GATED BRACHYTHERAPY

FIELD OF THE INVENTION

The present invention relates to brachytherapy.

BACKGROUND ART

Brachytherapy is a form of radiotherapy where a source of ionising radiation is placed inside or next to the area requiring treatment. It usually involves placing radionuclides in or close to a target in order to deliver radiotherapy. These can be injected into the patient and left in place permanently while the radioactivity decays, or removed after treatment is complete.

A variant of this is so-called high dose rate ("HDR") brachytherapy. This is administered by inserting one or more catheters into the body to pre-defined (planned) positions in the body. A radioactive source is then propelled from a shielded container along to the end of each catheter for a predetermined time, and then withdrawn back into the shielded container. While the source is inside the patient, it delivers the therapeutic dose to the target. This will inevitably also deliver a dose to the surrounding tissue.

One particular application of HDR is referred to as "Accelerated Partial Breast Irradiation" ("APBI") in which a small, single breast tumour is surgically removed together with a "margin" of tissue beyond the tumour, leaving a cavity in the breast. To prevent tumour recurrence caused by any remaining microscopic malignant or pre-malignant cells in the tissue surrounding this cavity, a course of radiation therapy is applied to that tissue. In conventional radiation treatment, radiation is applied by external beam radiotherapy once a day for typically 5-8 weeks following surgery. With APBI using HDR, the treatment regime is accelerated to (typically) two treatments a day for just five days.

In one type of HDR treatment, a single Iridium-192 (Ir-192) HDR source is used to treat the breast. Either during or a few days after surgery, an applicator comprising a catheter surrounded at its distal end by an inflatable balloon is inserted into the cavity in the breast under local anaesthetic, and water is injected to inflate the balloon so that it fits snugly inside the cavity. The most well-known balloon applicator is called MammoSite, made by Hologic Corp. At each treatment session an HDR radioactive source is passed from its shielded container down the central catheter to specific positions in the balloon for specific periods of time, governed by the requirements of the treatment plan, to deliver the therapeutic radiation. The source is then completely withdrawn back into its shielded container. Typically the source is in place for between 5 and 20 minutes for each treatment session, depending on the age (and hence radioactivity) of the radionuclide and the requirements of the treatment plan. The inflated applicator remains in place within the breast until the final treatment session has finished, whereupon it is deflated and removed.

Recently a form of APBI treatment has been developed using a miniature X-ray tube instead of a radionuclide (the Xoft Axxent system). We will refer to this as "Electronic HDR" ("E-HDR"). The advantage of using an X-ray tube is that the radiation can be turned off when it is not needed, so it has considerable safety and convenience factors compared with conventional radionuclide based HDR. Xoft Inc and others have disclosed the concept of varying the tube voltage (and hence the energy spectrum of the emitted x-rays) and/or the current (and hence the dose rate) and/or the direction of the x-ray beam in such a way as to shape the distribution of the therapeutic radiation dose in order to minimise the dose to unaffected regions or critical organs.

The field of brachytherapy is distinct from that of external beam radiation therapy, which uses linear accelerators to deliver radiation from outside the body. In external beam radiation therapy various techniques have been developed for directing, collimating and operating the treatment beam (usually to turn it on and off) based on the path of the beam relative to the target and other regions of the patient, and the state of the patient including their breathing cycle. The aim of these has been to maximise the dose applied to the target region while minimising the dose to non-target regions and (in particular) to sensitive regions. These techniques include interventional methods which arrest breathing for certain periods (such as the Elekta Active Breathing Coordinator), and free breathing methods which measure lung volume, target position, or assumed surrogates for these and control the beam based on acceptance limits (eg the Varian RPM and Brainlab Exactrac systems).

SUMMARY OF THE INVENTION

During APBI treatment, radiation passes beyond the "target volume" and delivers radiation dose to the lungs and, especially in the case of treatment of the left breast, to the heart. The heart is particularly vulnerable to radiation, and cardiac failure caused by radiation and/or drug therapy is a major cause of death in breast cancer patients who have survived 10 or more years after treatment for breast cancer.

The quality of x-radiation (i.e. the energy spectrum) produced by a miniature x-ray tube is different from that produced by Ir-192 and typically has less penetration into tissue. This means that the radiation dose from the x-ray source is more heavily attenuated (absorbed) with distance, so for any particular patient geometry, the heart will receive less radiation dose from APBI using E-HDR than using HDR. This can be further mitigated in E-HDR by modifying the dose rate and energy when the tube is irradiating towards the heart, but will still require a compromise between providing a therapeutic dose to the target volume that lies between the tube and the heart and minimising unwanted dose to the heart.

Example treatment plans have been published showing how the physical dose to the heart is considerably reduced with E-HDR compared to HDR. However, there is an additional radiobiological factor that works against E-HDR. The radiobiological effectiveness ("RBE") of x-radiation under typical clinical treatment conditions is reported to be higher than that of Ir-192. This means that a particular physical dose from the E-HDR will have greater biological effect than the same physical dose from HDR with Ir-192. So although the heart receives a lower physical dose from E-HDR due to the lesser penetration, the dose that it does receive will have a more serious effect on the heart than the equivalent dose delivered by Ir-192. Accordingly, the dose reduction of E-HDR compared to Ir-192 needs to be very significant if benefits are to be realised.

The present invention therefore provides an apparatus for treatment by brachytherapy comprising an X-ray source sized for insertion into a patient, a respiration state monitor, and a control apparatus adapted to receive respiration state information from the respiration state monitor and control the output of the X-ray source; the control apparatus being arranged to operate the X-ray source at a first output level when the respiration state monitor indicates a degree of lung inflation above a first preset threshold and operate the X-ray source at a second and lower output level when the respiration state monitor indicates a degree of lung inflation below a second preset threshold.

The principle is to activate the source only when it is apparent from the respiration state that the distance between the source and the heart is near its maximum. In this way, the dose received by the heart is minimised. The control apparatus can thus be arranged to deactivate or substantially inhibit the x-ray source when the respiration state information indicates that the patient's heart is less than a pre-set distance from the source.

The X-ray source can comprise an x-ray tube, in which case the control apparatus is preferably arranged to gate the tube current to a signal derived from the respiration state monitor.

The respiration state monitor can comprise at least one of an external respiration surrogate, an internal marker of heart position, an internal marker of source position, a direct measure of lung volume, an indirect measure of lung volume, or a breath hold prompt.

For simplicity, the first and second thresholds can be the same, although more complex modulation of the output of the x-ray source is possible. The second output level is preferably zero, although a sufficiently low output should be effective in reducing the dose to the heart to an acceptable level.

In another aspect, the present invention provides an apparatus for treatment by brachytherapy comprising an X-ray source sized for insertion into a patient, a breath hold prompt, and a control apparatus adapted to control the breath hold prompt and the output of the X-ray source, by activating the X-ray source only when the breath hold prompt is active.

BRIEF DESCRIPTION OF THE DRAWINGS

An embodiment of the present invention will now be described by way of example, with reference to the accompanying figures in which.

DETAILED DESCRIPTION OF THE EMBODIMENTS

Figure 1:
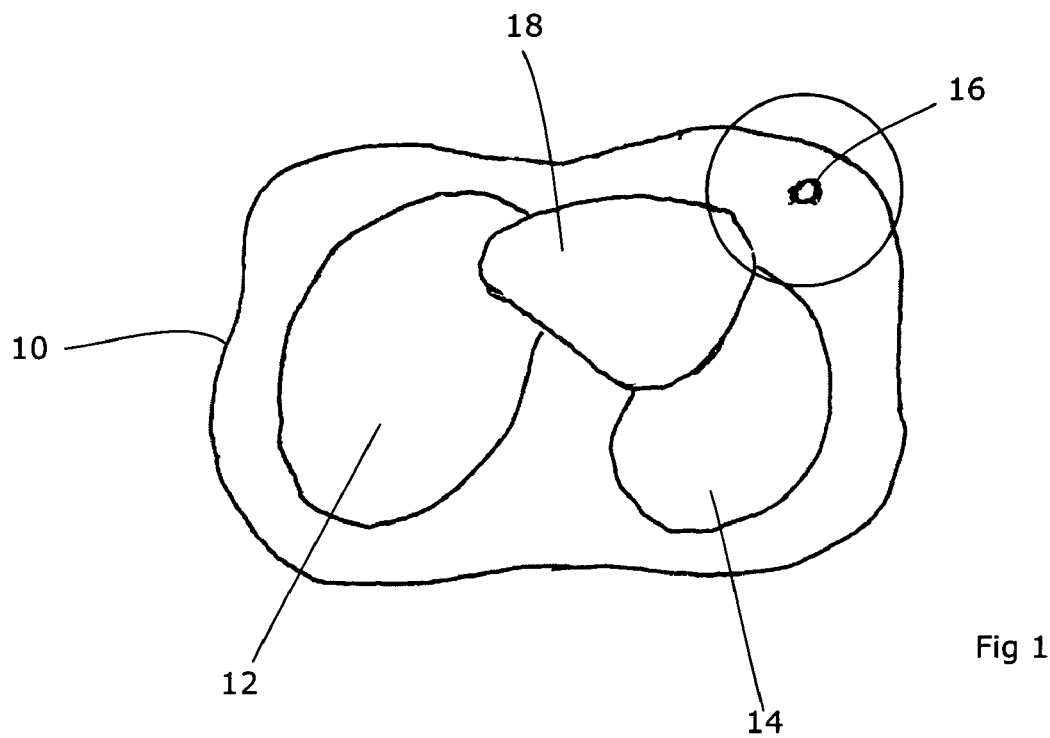
FIG. 1 shows a transverse section through a patient illustrating the relative position of the heart, the lung, and a tumour site at an exhalation point of the respiratory cycle.
Figure 2:
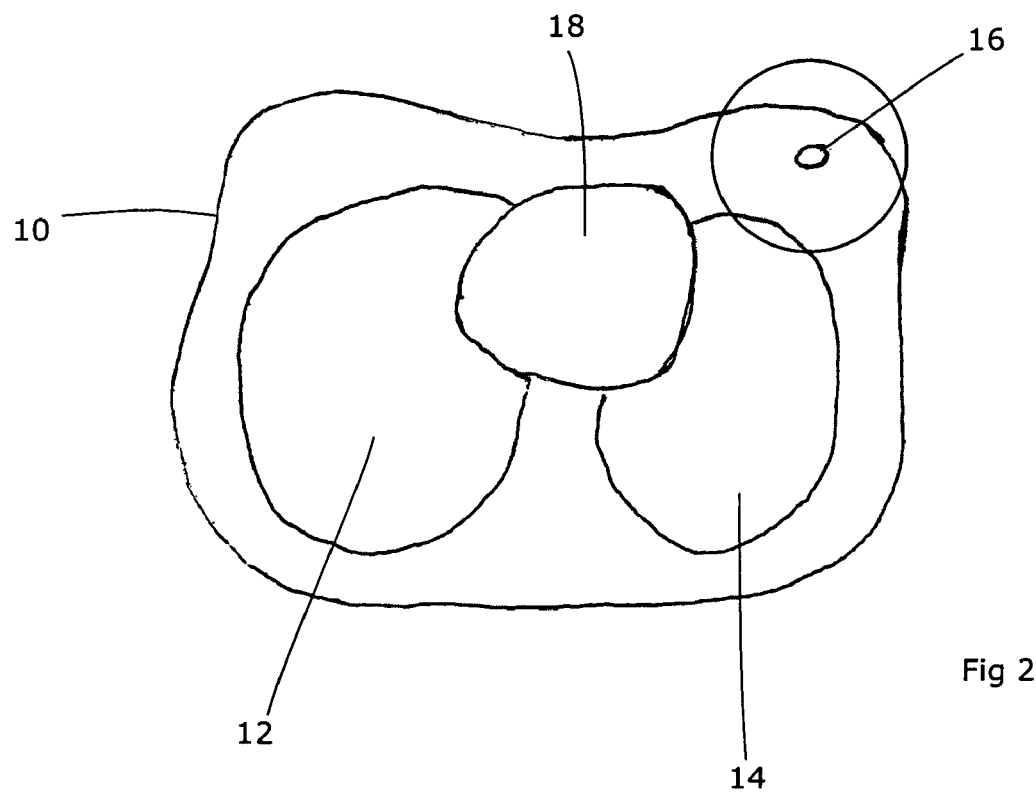
FIG. 2 shows a transverse section through a patient illustrating the relative position of the heart, the lung, and a tumour site at an inhalation point of the respiratory cycle.

The invention exploits the following facts/features to reduce the radiation dose to the heart:
a) E-HDR dose rate falls off rapidly with distance
b) E-HDR radiation can be turned on and off quickly
c) The heart is moved away from the left breast when a patient inhales By only turning on the radiation beam when the heart is near its maximum distance from the radiation source, the radiation to the heart will be further minimised. This is shown in FIGS. 1 and 2, which show a section through a patient 10 in the exhaled and inhaled state respectively. The right lung 12 and the left lung 14 are visible, as is the heart 18 and a volume 16 from which a tumour has been surgically removed leaving a void. Also shown in FIGS. 1 and 2 are the 5% dose levels for an x-ray source located in the volume 16; these cover the target volume for the radiation, i.e. the breast tissue surrounding volume 16. It can be seen that in the exhaled state shown in FIG. 1, this overlaps with the heart 18 whereas in the inhaled state shown in FIG. 2 the heart lies outside this range and is therefore subjected to a lesser dose.

Figure 3:
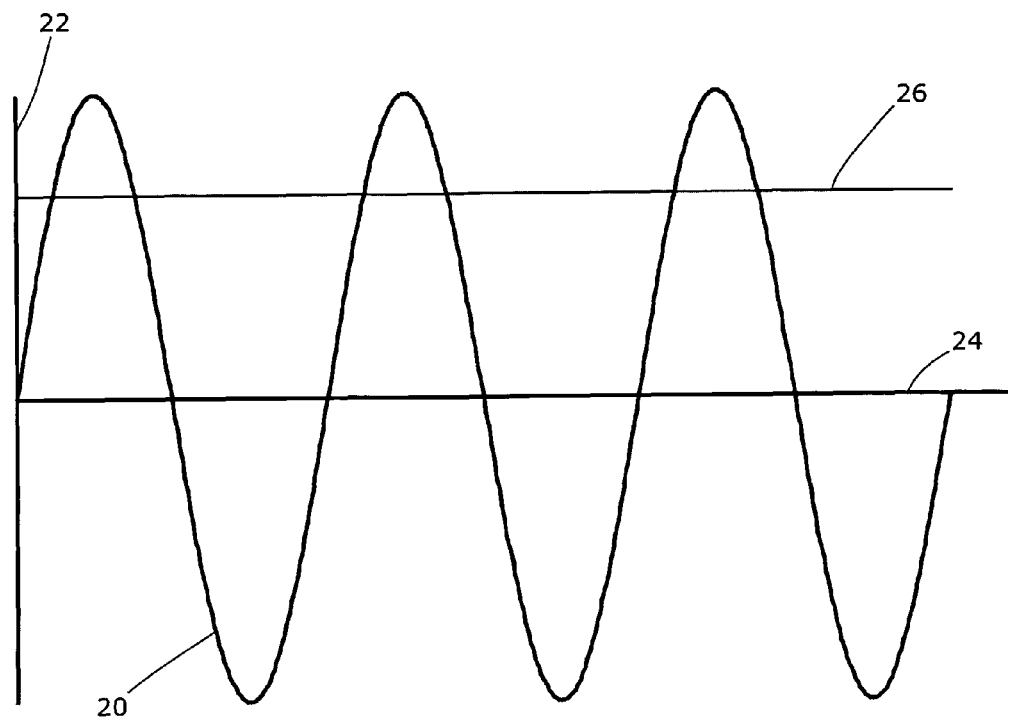
FIG. 3 shows an idealised respiratory cycle.

This means that the relatively fast switching of an E-HDR source can be used as shown in FIG. 3. An idealised respiration cycle 20 is depicted, in which the degree of lung filling (shown on the Y axis 22) varies with time along the x axis 24. The respiration cycle of a patient can be measured or controlled in a variety of ways that will be apparent to those skilled in the art. Assuming that the cycle is not manipulated but is allowed to continue uninterrupted, by setting a threshold level 26 it is possible to create a signal indicating when the lung filling is greater than a certain degree. As is apparent from FIGS. 1 and 2, this correlates generally to a maximum separation of the heart and the target volume. This can then be used in E-HDR by gating the tube current (and hence the radiation) to such a signal.

Generally, the signal is required to indicate when the heart is more than a pre-set distance from the source. Thus, other forms of useful signal may include measurements via an external surrogate or an internal marker of the heart and/or source position itself, or by a direct or indirect measure of lung volume. Alternatively, a breath hold (assisted or otherwise) can be employed, and the tube current gated to the breath hold prompt or to a breath hold report.

Figure 4:
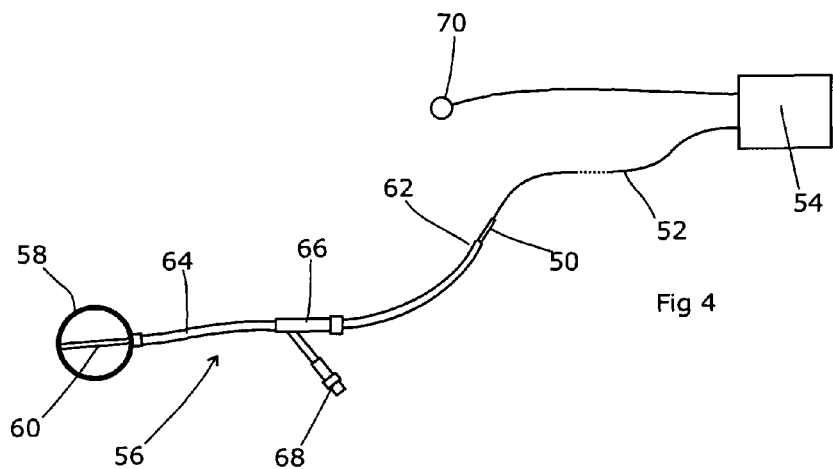
FIG. 4 shows apparatus for delivering an E-HDR source.

FIG. 4 illustrates apparatus embodying the invention. A miniature x-ray tube 50 is supplied with current (etc) via a flexible cable 52 which leads back to a control unit 54. The x-ray tube is insertable into an implant 56; this comprises an inflatable balloon 58 around the end of a catheter 60, the other end 62 of which is open to allow entry of the x-ray tube 50. A concentric outer sleeve 64 is provided outside the catheter 60 and communicates with the interior of the balloon 58. This sleeve extends from the balloon 58 to a tap 66 part-way along the catheter 60 with a valve 68 via which a fluid can be injected or withdrawn in order to inflate or deflate the balloon 58.

Thus, following removal of a tumour from the volume 16, the catheter can be inserted until the deflated balloon is within the void left at the tumour site, and a fluid such as water injected via the valve 68 to inflate the balloon 58 and occupy the void. The x-ray tube 50 can then be inserted along the catheter 60, pushed via the cable 52 until it lies at one or more predefined treatment positions within the end region of the catheter inside the void. The x-ray tube can then be activated by the control unit 54.

A respiration state monitor is generally depicted as item 70. As indicated above, this can be a simple breath hold prompt which indicates to the patient that they should hold their breath in; in this case the control unit 54 will activate the breath hold prompt, activate the x-ray tube 50 for a preset period, de-activate the x-ray tube 50, then de-activate the breath hold prompt, and allow the patient to breath again before repeating the process as required.

Alternatively, the respiration state monitor 70 can be an active device taking information from the patient as to their respiration state and feeding this back to the control unit 54, which will then activate and de-activate the x-ray tube 50 as required in order to correlate doses with periods of lung inflation.

Generally, the respiration state monitor 70 can be according to any of the arrangements disclosed herein, or otherwise, such as to permit the control unit 54 to activate and de-activate the x-ray tube 50 in substantial synchrony with periods of the respiratory cycle in which the distance between the heart or other sensitive organs and the irradiation site is maximised.

The use of breath hold or gating to maximize the distance of the heart from the left breast is novel in the context of brachytherapy. It would be difficult to achieve this using conventional HDR because of the need to stop and restart irradiation repeatedly in a short timescale. Inserting and removing the source breath-by-breath would be technically difficult, would increase the likelihood of equipment failure, and would expose the tissue surrounding the entrance/exit route to extra radiation dose. It would also be difficult to apply adequate shielding to cover and expose the source in-situ between breaths; such shielding would be bulky, heavy and impractical.

This technique, i.e. for increasing the distance between source to normal tissue for a radiation source inside the body which can be switched on and off, is not restricted to treatments of the breast, nor to just protecting the heart. For example, the techniques could be used to reduce dose to the spinal cord or the heart when a miniature x-ray tube is introduced into the lung, or during treatment of the vessels of the heart (for example for treatment of hyperplasia) in order to spare other organs.

In the above discussion, we describe the de-activation of the x-ray tube when lung inflation is below a certain threshold. Although this is the preferred option, an alternative method would be to reduce the dose rate and/or the energy from the x-ray tube, rather than de-activate it completely, when lung inflation is below the threshold. This would reduce the dose applied to regions such as the heart to levels that may be considered acceptable.

It will of course be understood that many variations may be made to the above-described embodiment without departing from the scope of the present invention.

The invention claimed is:

1. Apparatus for treatment by brachytherapy comprising an X-ray source sized for insertion into a patient, a respiration state monitor, and a control apparatus adapted to receive respiration state information from the respiration state monitor and control the output of the X-ray source; the control apparatus being arranged to operate the X-ray source at a first output level when the respiration state monitor indicates a degree of lung inflation above a first preset threshold and operate the X-ray source at a second and lower output level when the respiration state monitor indicates a degree of lung inflation below a second preset threshold.

2. Apparatus according to claim 1 in which the X-ray source comprises an X-ray tube.

3. Apparatus according to claim 2 in which the control apparatus is arranged to gate the tube current to a signal derived from the respiration state monitor.

4. Apparatus according to claim 1 in which the control apparatus deactivates the X-ray source when the respiration state information indicates that the patient's heart is more than a pre-set distance from the source.

5. Apparatus according to claim 1 in which the respiration state monitor comprises at least one selected from the list consisting of an external respiration surrogate, an internal marker of heart position, an internal marker of source position, a direct measure of lung volume, an indirect measure of lung volume, and a breath hold prompt.

6. Apparatus according to claim 1 in which the first and the second preset thresholds are the same.

7. Apparatus according to claim 1 in which the second output level is substantially zero.

8. Apparatus for treatment by brachytherapy comprising an X-ray source sized for insertion into a patient, a breath hold prompt, and a control apparatus adapted to control the breath hold prompt and the output of the X-ray source, by activating the X-ray source only when the breath hold prompt is active.

* * * * *